United States Patent [19]

Houghton et al.

[11] Patent Number: 5,714,439
[45] Date of Patent: Feb. 3, 1998

[54] PROPANIL DISPERSIBLE GRANULE

[75] Inventors: Richard David Houghton, Harleysville; Linda Louise Graham, Flourtown; David Prescott Krutsch, Bethayres, all of Pa.

[73] Assignee: Rohm and Haas Company, Philadelphia, Pa.

[21] Appl. No.: 653,962

[22] Filed: May 28, 1996

Related U.S. Application Data

[63] Continuation-in-part of Ser. No. 465,066, Jun. 6, 1995, Pat. No. 5,532,209, which is a continuation of Ser. No. 887,422, May 21, 1992, abandoned, which is a continuation of Ser. No. 606,642, Oct. 31, 1990, abandoned.

[51] Int. Cl.$^6$ .......................... A01N 37/22; A01N 25/12
[52] U.S. Cl. ................................................ 504/339
[58] Field of Search ........................................ 504/339

[56] References Cited

U.S. PATENT DOCUMENTS

| | | | |
|---|---|---|---|
| 3,617,246 | 11/1971 | Duyfjes | 71/79 |
| 3,920,442 | 11/1975 | Albert et al. | 71/92 |
| 3,954,439 | 5/1976 | Papamichael et al. | 71/93 |
| 4,197,112 | 4/1980 | Albert et al. | 71/93 |
| 4,280,833 | 7/1981 | Beestman et al. | 71/100 |
| 4,411,692 | 10/1983 | LeClair et al. | 71/93 |
| 4,870,065 | 9/1989 | Balogh et al. | 514/119 |
| 4,936,901 | 6/1990 | Surgant | 71/92 |

FOREIGN PATENT DOCUMENTS

| | | |
|---|---|---|
| 252896 | 8/1987 | European Pat. Off. |
| 1433882 | 1/1973 | United Kingdom . |
| 8900079 | 1/1989 | WIPO . |

*Primary Examiner*—S. Mark Clardy
*Attorney, Agent, or Firm*—Thomas D. Rogerson

[57] ABSTRACT

A dispersible granular formulation has been developed which contains at least 60% propanil herbicide. This formulation also provides excellent suspensibility and dispensability characteristics and resists attrition.

8 Claims, No Drawings

PROPANIL DISPERSIBLE GRANULE

This application is a continuation-in-part of U.S. patent application Ser. No. 08/465,066 filed Jun. 6, 1995, now U.S. Pat. No. 5,532,209 which is a continuation of Ser. No. 07/887,422, filed May 21, 1992, now abandoned, which is a continuation of application Ser. No. 07/606,642, filed Oct. 31, 1990 now abandoned.

This invention relates to novel water dispersible granule formulations of the herbicide propanil (N-(3,4-dichlorophenyl)propionamide) and processes for their preparation.

Water dispersible granular pesticide formulations are known. These formulations are desirable because they avoid the use of potentially toxic solvents and permit the use of easily-disposable paper containers or water soluble containers. In addition, such formulations are less dusty than wettable powder formulation. As a result, potential exposure of pesticide applicators and the general public to the pesticide or solvent is thereby reduced.

Typical dispersible granular pesticide formulations are described for example in GB 1,433,882, EP 0,252,896 and U.S. Pat. No. 3,920,442. GB 1,433,882 describes a process for preparing dispersible granules by blending premilled, water-insoluble, active ingredient, dispersing agents, disintegrating agent and wetting agents in an aqueous suspension. The aqueous mix is extruded to form granules which are then dried to yield the final product. U.S. Pat. No. 3,920,442 describes water dispersible pesticide aggregates containing 5 to 95% by weight of pesticide. The aggregates are prepared by contacting the finely divided solid ingredients in a fluidized bed with a fine spray of water or a solution of the binder-dispersant followed by drying.

In attempts at making pesticide granules, it has often been found that granules of agglomerates prepared from the formulated wettable powders of the art using well-known agglomerating techniques and using water as the agglomerating agent, are not easily dispersible in water. On the other hand, agglomerates which are readily water-dispersible are often not sufficiently resistant to attrition and form a fine dust fraction upon handling and shipping. If conventional binders are added to make the granules strong, then they are not dispersible in water. Techniques such as tabletting, extrusion and rolling which involve high-pressure compacting of moistened mixtures containing finely divided pesticides, diluents, binder and dispersant, as described in U.S. Pat. No. 3,617,246, lead to dense pellets, tablets, plates, and rods which are subsequently dried and crushed. These techniques have also been used to form granules containing up to 50% of active pesticide, but the resulting granules are not rapidly or completely water dispersible and are not suitable for use in preparing sprayable suspensions.

Low-melting solids such as propanil present an especially difficult problem in the preparation of a dispersible granule formulation. The low-melting solid, herein defined as melting below 100° C., tends to melt or become sticky during or subsequent to the grinding or milling process which is a necessary step in preparing dispersible granules. Partially due to its low melting point, it has not heretofore been possible to produce a propanil dispersible granular product which combines the features of a high active ingredient content, good suspensibility and dispersant properties, as well as resistance to attrition thereby avoiding the formulation of a dust. EP 0,252,896 describes a possible solution to this problem which requires micro-encapsulation of low-melting pesticides prior to granulation. However, microencapsulation involves additional processing steps and adds to the cost of the overall formulation.

Commercial formulations of propanil dispersible granules are available, but these products have deficiencies in that the active ingredient content is relatively low and/or they fail to provide adequate suspension or dispersibility characteristics or are not resistant to attrition.

A dispersible granule herbicide composition designed for dispersion in a liquid carrier should ideally have a high content of active material, should resistant to mechanical breakdown into a dust (attrition), should be readily dispersible in the carrier and should then form a dispersion which is as stable as possible, requiring a minimum of subsequent agitation to maintain homogeneity. The liquid carrier will, of course, for convenience normally be water. We have now devised a way to make granules which readily break down when they are stirred into a liquid carrier to give a stable dispersion of the active ingredient.

This invention relates to dispersible granule formulations of propanil herbicide and processes for preparing these formulations including pan granulation or extrusion of a pre-wet mixture comprising finely-ground active ingredient, wetting agent, dispersing agent and carrier. The dispersible granules produced by these processes contain at least 60% propanil, preferably at least 80% propanil. They also have a suspensibility of at least 70%, preferably at least 80%, when measured according to the procedure of the Collaborative International Pesticides Analytical Council (CIPAC) Handbook, Vol. 1, Ed. G. R. RAW (1970), Method Number MT 15.1 using standard hard water (342 ppm as calcium carbonate, also known as Army Hard Water) prepared according to CIPAC method MT 18.1.4, as a 0.9% to 2.0% weight/volume dispersion. An important advantage of the dispersible granules is that after 10 minutes of attrition the granules form less than 0.3% by weight of particles less than 45 microns in diameter.

The dispersible granules of this invention are prepared by a process comprising the steps of:

a) forming a premix by milling, at a temperature of less than 80° C., one or more surfactants combined with an amount of propanil sufficient to achieve at least 60% active ingredient in said dispersible granules to a particle size of less than 20 microns preferably less than 15 microns and more preferably less than 10 microns;

b) adding to said premix less than 25% water, optionally adding a wetting agent;

c) mixing until a paste is obtained;

d) granulating said paste; and e) drying the granules thus produced.

By forming the premix and milling at a temperature of less than 80° C., many of the problems related to processing the low-melting propanil are avoided.

The term "dispersible granule" or "DG" means granules substantially all of which have a mean particle size of at least 1 mm., i.e. a particle size much larger than the mean particle size of a powder, the mean particle size of which is measured in microns. When referring to the particle size of a powder in this application, the size specified is that of the 90th percentile particles.

"Attrition" as used in this application is defined as reduction in particle size which occurs when propanil granules are shaken with steel balls as described in Example 1(c)(3).

The term "granulating" means the process of agglomeration of the components of the paste accomplished by any of the standard agglomeration techniques such as tabletting, pan agglomeration, or extrusion. Extrusion is the preferred method.

Suspensibility of the granule produced is proportional to the amount of water added to the premix prior to extrusion.

The amount of water added may produce a paste with a consistency from that of a moist powder to dough-like. However, addition of too much water will cause sticking of the extrudate as it exits the extruder. The relationship of water content of premix and suspensibility is shown in the table below.

| Parts Water per 100 parts premix | % Suspensibility |
|---|---|
| 8 | 63.1 |
| 14 | 78.4 |
| 18 | 84.6 |

The preferred amount of water to be added to the premix is 18 to 20 parts per 100 parts of premix.

After extrusion the dispersible granules are dried. For storage stability, it is important to reduce the residual water to at least 2% and preferably below 1%. High drying temperatures are injurious to the product. The preferred drying temperature is less than 60° C. and more preferably less than 40° C. Drying may be accomplished by any suitable drying means which supplies heated gas, preferably air, at a controlled temperature. A two stage fluid bed dryer is preferred.

A preferred process for producing the propanil dispersible granules of this invention comprises the steps of:

a) forming a premix by milling, at a temperature of less than 80° C., a mixture of propanil, dispersant and flow aid to a particle size between 3 and 15 microns;

b) adding a wetting agent dissolved in 12–20% water (based on the total weight of ingredients of step (a)) to the milled mixture;

c) mixing until a homogeneous, extrudable paste is obtained;

d) extruding the paste obtained in step c) to produce extruded granules;

e) drying the extruded granules at a temperature of less than 60° C. to a moisture content of less than 2%.

In addition to the active ingredient, propanil, the mixture to be formed into dispersible granules will contain one or more surfactants and, optionally, flow enhancing agents, dispersants, wetting agents and defoaming agents.

The term "surfactant" is used in the broad sense to include materials which may be referred to as emulsifying agents, dispersing agents and wetting agents, and the surfactant component may comprise one or more surfactants selected from the anionic, cationic and nonionic type. Examples of surfactants of the anionic type include soaps, salts of aliphatic monoesters of sulfuric acid such as sodium lauryl sulfate, salts of sulfonated aromatic compounds, for example sodium dodecylbenzene sulfonate, sodium, calcium or ammonium lignosulfonate or butylnaphthalene sulfonate, and a mixture of the sodium salts of diisopropyl- and triiso-propylnapthalene sulfonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters with ethylene oxide and the lecithins and phosphorylated surfactants such as phosphorylated ethylene oxide/propylene oxide block copolymer and ethyoxylated and phosphorylated styryl substituted phenol.

Preferably the surfactant component will comprise at least one wetting agent such as those selected from alkyl naphthalene sulfonates, alkylaryl polyoxyethylene ammonium sulfonates phosphate esters, sulfosuccinates and nonionics such as tridecyl alcohol ethoxylate; and/or at least one dispersing agent such as those selected from the group of napthalene sulfonates, lignosulfonates, polyacrylates and phosphate esters.

Typically the total surfactant component will comprise from 0.1 to 25% and preferably from 1 to 15% by weight of the dry weight of the dispersible granule.

In the context of this specification a dispersing agent is a surfactant agent which facilitates the dispersion of the pesticide particles when the product is added to a liquid, for example water. The dispersing agents used are preferably water-soluble ones. Examples of dispersants preferred for the dispersible granule formulations of this invention include: Tamol 731®, Polyfon®H, Polyfon O, Reax® 88B, Morwet® D-425, Reax 45DA, Polyfon T, Polyfon F, Polyfon H, Lignosol™ XD-65, Reax 45L Reax 85A, Reax 910, Polyfon OD, PC-825 Polyfon T, and Stepsperse® DF 500. Most preferred dispersants are: Reax 85A, Polyfon H, and Stepsperse® DF 500.

Examples of surfactants preferred as wetting agents for the dispersible granule formulations of this invention include Morwet® B, Morwet EFW, Sellogen® DFL, Morwet IP, Igepon® AC-78, Igepon T-77, Aerosol OT-B, and Surfactant XN-45S. Most preferred wetting agents are Morwet B and Surfactant XN-45S.

All surfactants act as dispersing agents in some degree, and also in some degree as wetting agents; most surface-active agents are however, more efficient in one capacity than the other. The worker of ordinary skill in the formulation art can select a surfactant most suitable for the purpose in view.

Small particles of a low-melting solid such as propanil often tend to stick together thereby causing flow problems in processing the material. Flow aids such as clays or silica particles may be used to minimize these problems. Flow aids preferred for the propanil dispersible granular include HiSil® 233, Wessalon® 50S, Cab O-Sil® M5, Wessalon S, Barden® Clay, and Microcel® E. Most preferred are HiSil 233 and Wessalon 50S. The flow aid content of the dispersible granule may vary from 0 to 10% and preferably from 1 to 8%.

Addition of a defoaming/antifoaming ("defoaming") agent is desirable to aid in the processing and use of the dispersible granules. Defoaming agents may be used in amounts of 0.1% to 5%; a preferred defoaming agent is Emery 2895.

Disintegrants, which are water soluble, organic compounds such as starch or sugar or inorganic salts such as sodium acetate or sodium bicarbonate, are sometimes used in dispersible granule formulations. See GB 1,433,882 for example. We have found that these disintegrants have adverse effects on the propanil dispersible granules of this invention. Formulations containing disintegrants were found to be more dusty and disperse less effectively than the granules of this invention.

Dust is herein defined as particles with diameter less than 45 microns. A solid having less than 0.3% by weight dust is defined as "non-dusty" while a solid with more than 4% dust is defined as "very dusty". Solids with 0.3–4% dust are defined as "dusty". Dust content and resistance to attrition of the propanil dispersible granules of this invention are minimized by forming the granules by the preferred mode of extrusion.

The most preferred composition of this invention comprises by weight percent: propanil 80%; dispersant, Reax 85A+Stepsperse® DF 500, 9.2%; flow aid, HiSil, 4.0%; wetting agent, surfactant XN-45S, 2.0%; defoaming agent, Emery 2895, 0.5%; and water, less than 1%.

Examples of dispersants, wetting agents, flow aids, and defoaming agents useful in this invention are shown in the following table.

| | Producer | Chemical Type |
|---|---|---|
| Dispersants | | |
| Tamol® 731 | Rohm and Haas Co. Philadelphia, PA 19106 | Sodium carboxylate polyelectrolyte |
| Polyfon® H | Westvaco Chemicals | Aliphatic and aromatic sulfonated lignin |
| Polyfon F | P.O. Box 70848 | |
| Polyfon T | Charleston Hts., SC | |
| Polyfon O | 29415-0848 | |
| Polyfon OD | | |
| Reax® 88B | | |
| Reax 45DA | | |
| Reax 45L | | |
| Reax 85A | | |
| Reax 910 | | |
| Lignosol XD-65 | Reed Lignin, Inc. 81 Holly Hill Lane Greenwich, CT 06830 | Sodium lignosulfonate |
| Stepsperse® DF 500 | Stepan Company Edens & Winnetka Rds Northfield, IL 60093 | Sodium lignosulfonate |
| Wetting Agents | | |
| Morwet® B | DeSoto, Inc. 2001 N. Grove Fort Worth, TX 76113 | Sodium n-butyl naphthalene sulfonate |
| Morwet EFW | | Naphthelene sulfonate |
| Morwet IP | | Sodium diisopropyl napthalene sulfonate |
| Sellogen® DFL | Diamond Shamrock 350 Mt. Kemble Ave. Morristown, NJ 07960 | Alkyl naphthalene sulfonate |
| Igepon® AC-78 | GAF Corp. 140 W. 51st. St. New York, NY 10020 | Sodium cocoyl isethionate |
| Igepon T-77 | | Sodium methyl oleoyl taurate |
| Aerosol OT-B | American Cyanamid | Sodium dioctyl sulfo succinate |
| Surfactant XN-45S | Rohm and Haas Co. Philadelphia, PA 19106 | Ammonium alkyl/aryl polyoxyethylene sulfate |
| Flow Aids | | |
| HiSil® 233 | PPG Industries One Gateway Center Pittsburgh, PA 15222 | Silica |
| Wessalon® 505 | Degussa Corp. Rt. 46, Hollister Rd. Teterboro, NJ 07608 | Silica |
| Wessalon S | | Silica |
| Cab-O-Sil® M-5 | Cabot Corp. Boston, MA 02110 | Silica |
| Barden® Clay | J. M. Huber Corp. Rt. #4 Macon, GA 30201 | Clay |
| Microcel® E | Johns-Mansville P.O. Box 5108 Denver, CO 80217 | Silicate |
| Defoaming Agents | | |
| Mazu DF 1300 | Mazer Chemicals 3938 Poreti Drive Gurnee, IL 60031 | Silicone and Silica |
| Emery 2895 | Henkel Corp. 300 Brookside Ave. Ambler, PA 19002 | Fatty acid |

Some embodiments of this invention are described in the following examples:

EXAMPLE 1

Preparation of Propanil 80 DG a) Preparation of a Premix

Technical propanil (97%) was melted by heating at 110° C. for 24 hours. The molten material was then poured into aluminum foil lined trays to a depth of about one inch. After cooling at room temperature for 24 hours, the solid was broken up and milled in a coffee mill. The ground material classified as follows:

| Mesh Size | Weight % |
|---|---|
| Larger than 4 mesh | 14.9 |
| 4 to 10 mesh | 40.5 |
| 10 to 20 mesh | 29.3 |
| 20 to 50 mesh | 8.3 |

The coarse milled propanil was blended with other formulation ingredients in a Marion mixer (Mfg. for Rapid Machinery Co., Marion Mixer, Iowa by Texas Div. Tranter Inc. Old Burk Road, Wichita Falls, Tex.) in the following ratio of ingredients:

| Ingredients | Weight % |
|---|---|
| Propanil | 89.5 |
| Reax 85A | 9.5 |
| HiSil 233 | 4.1 |
| Mazu DF-1300 | 0.5 |
| Total | 100.0 | and mixed for 20 minutes.

The above blend was transferred to a Bantam micropulverizer (Mikropul, 10 Chantaur Road, Summit, N.J. 07901) fitted with a 0.42 inch screen and automatic feed; the grinding chamber was cooled with dry ice. The mean particle size of micropulverized product was 43.8 microns. The micropulverized product was then air milled in an 8" horizontal (pancake) jet mill (Fluid Energy Processing and Equipment Co., 153 Penn Energy, Hatfield, Pa. 19440). An Accu-Rate feeder (Accurate Feeder, 746 E. Milwaukee Street, White Water, Wis. 53190) was fitted with a 2" screw feed nozzle positioned to deliver micropulverized material to the air mill. High pressure nitrogen was used for both feeding and grinding to maintain an oxygen concentration below 10%. The ground material was collected in the air bag.

| Air Mill Operating Conditions | |
|---|---|
| Nitrogen feed pressure | 65 psig |
| Nitrogen grind pressure | 60 psig |
| Accurate-rate setting | 100 |

Under these conditions the milling rate was 8–10 lbs./hour. The mean particle size was 9.1 microns. This product constituted propanil 80 DG premix.

b) Preparation of the dispersible granule

Propanil premix (98.0 parts by weight), Surfactant XN-45S (60% aqueous solution, 3.33 parts by weight) and water (16.67 parts by weight) were mixed in a Kitchen Aid mixer (Hobart, Kitchen Aid Div. Troy, Ohio) for approximately 2–3 minutes to form a paste.

The paste was transferred to a KAR 130 extruder (Tsu Tsui Rikagaku Kikai Co., Ltd., Japan) fitted with a 1.0 mm screen and extruded. After extrusion, the extrudate was air dried to a moisture content of 1-2% at a temperature of less than 40° C.

c) Measurement of Physical Properties

1. Suspensibility (variation of CIPAC method in duplicate)

One gram of propanil DG was placed in a glass-stoppered graduated cylinder containing 99 ml of Army Hard Water at 25°. The cylinder was inverted 30 times over a period of 90 seconds and allowed to stand for 30 minutes. The bottom 10 ml was separated, evaporated and dried for 48 hours at 60° C.; and the resulting residue was used to calculate suspensibility using the following formula.

% suspensibility=[1—weight of residue]×111

This test indicated that the product produced had a suspensibility of 88.4% and 88.8% (ave.=88.6%).

2. Product Attrition Measurement

Ten ⅜ inch steel balls and 50 g propanil DG were placed in the bottom pan of 8 inch diameter stainless steel sieves. The pan was shaken on a Ro-tap sieve shaker with a hammer tapper for 10 minutes. The steel balls were removed from the pan and the granules were transferred to the top of the nested sieves in the order of 20, 60, 100, 200, 325 mesh and bottom pan. The nested screens were inserted into the Ro-top and shaken for 15 minutes. The amount of residue on each sieve and bottom pan was determined. The weight percent of each fraction was determined by sieving before and after the attrition test.

Results of the measurements were as follows:

|  | Part. Cut | Sieve Test (Before) | Attrit. Test (After) | Differ. |
|---|---|---|---|---|
| Through a 325 mesh | <44 um | 0.20 | 0.20 | 0.0 |
| Retained on 325 mesh | 44/74 | 0.16 | 0.14 | −0.02 |
| Retained on 200 mesh | 74/149 | 0.08 | 0.18 | 0.10 |
| Retained on 100 mesh | 149/250 | 0.02 | 1.21 | 1.19 |
| Retained on 60 mesh | 250/840 | 0.10 | 1.23 | 1.13 |
| Retained on 20 mesh | >840 um | 99.44 | 97.04 | −2.40 |
|  |  | 100.00% | 100.00% |  |

These results indicate that there was an increase of 2.4% in particles less than 840 um in size following the attrition test. This increase was confined to particles within the range of 250 um to 74 um. No increase of percent particles below 44 um occurred. Initial percentage below 44 um was 0.2%.

3. Residual Moisture loss (in duplicate)

Approximately 5 grams DG was weighed to the nearest 0.01 g in a pre weighed pan, and dried 24 hours (+1 hour) at 60° C. at approximately 15 mm Hg pressure. The percent moisture loss was measured by weighing the residue. Duplicate measurements indicated moisture losses of 1.1% and 1.5% (ave.=1.3%).

4. Disintegration/Suspensibility (specified in GB 1,433,882 on pg. 4)

One gram DG was added to 100 ml Army Hard Water in a centrifuge tube and inverted 15 times slowly. The tube was then placed in a 30° C. water bath and readings (ml of sediment) were taken at 2, 5, 30 minutes. After 30 minutes the suspension was poured through a 120 mesh screen. The screen was washed with 1 liter water and the residue weight was noted. The results were follows:

| Time | ml Sediment | Screen Residue g. |
|---|---|---|
| 2 min | 0.05 | 0 |
| 5 min | 0.1 | 0 |
| 30 min | 0.3 | 0 |

EXAMPLE 2

A number of formulations of propanil DG were prepared with active ingredient content ranging from 60.4% to 90.2%. The procedure for preparing these granular formulations followed the general procedure of Example 1, except that Morwet B, Polyfon H and Barden Clay were substituted for Surfactant XN-45S, Reax 85A and HiSil 233, respectively. No antifoam agent was used. The results are shown in the table below.

| Ingredients as WT. % | | | | | | | | |
|---|---|---|---|---|---|---|---|---|
| Propanil Tech. | 60.4 | 65.4 | 70.4 | 75.4 | 75.4 | 80.2 | 85.2 | 90.2 |
| Morwet B | 2.0 | 2.0 | 2.0 | 2.0 | 2.0 | 2.0 | 2.0 | 2.0 |
| Polyfon H | 10.0 | 10.0 | 10.0 | 10.0 | 21.1 | 16.2 | 11.1 | 6.0 |
| Barden Clay | 26.5 | 21.3 | 16.2 | 11.1 | 0 | 0 | 0 | 0 |
| Total | 100 | 100 | 100 | 100 | 100 | 100 | 100 | 100 |
| Suspensibility (%) | 91.7 | 100 | 100 | 100 | 100 | 92.7 | 64.5 | 14.0 |

EXAMPLE 3

Comparison with Competitive products

1. Comparison of propanil DG with formulations incorporating disintegrants as described in British Patent 1,433,882

Propanil 80DG was prepared with 0, 2, and 4 percent of the disintegrants sodium bicarbonate and sodium acetate. Various physical properties were measured using air dried, extruded product. Use of disintegrants, at either level, worsened dispersibility in water although there was some slight improvement in suspensibility with 2 percent sodium bicarbonate or 4 percent sodium acetate after 2 and 5 minutes. Samples containing sodium acetate required additional water in the wetting step to allow proper extrusion.

Procedure

Using Propanil 80DG premix (milled but not extruded), a control and alternative extruded formulations containing 2 and 4 percent disintegrants were made. These were prepared according to the procedure of Example 1 and all compositions used 2 percent (solids) Surfactant XN-45S in the wetting step at the rate of 18:100 water to premix. The complete compositions were:

| Composition | Propanil DG Control | GB 1,433,882 Disintigrants | | | |
|---|---|---|---|---|---|
|  |  | 1 | 2 | 3 | 4 |
| Propanil Premix* | 98.0 | 96.0 | 94.0 | 96.0 | 94.0 |
| Surfactant XN-45S (60%) | 3.33 | 3.33 | 3.33 | 3.33 | 3.33 |
| Water | 16.67 | 16.67 | 16.67 | 16.67 | 16.67 |
| Total Parts | 118.0 | 118.0 | 118.0 | 118.0 | 118.0 |

-continued

| Composition | Propanil DG Control | GB 1,433,882 Disintigrants | | | |
|---|---|---|---|---|---|
| | | 1 | 2 | 3 | 4 |
| % Sodium bicarbonate (anhy.) | — | 2.0 | 4.0 | — | — |
| % Sodium acetate (anhy.) | — | — | — | 2.0 | 4.0 |
| % Water to aid extrusion | 0 | 2.5 | 3.4 | 4.0 | 6.0 |

*Propanil premix composition:

| | Weight % |
|---|---|
| Propanil | 85.9 |
| HiSil 233 | 4.1 |
| Mazu DF-1300 | 0.51 |
| Reax 85 A | 9.5 |
| Total | 100.0 |

The premix and disintegrants, sodium bicarbonate or sodium acetate were mixed together in a Kitchen Aid mixer for approximately 1 minute. The surfactant/water solution was added while mixing and allowed to knead for 2-3 min. Initial compositions with disintegrants which were formulated with the same concentration of water as the control were too dry for extrusion (extrusion process did not form noodles). Additional water was added as indicated in the above table and kneading continued for an additional 1-2 min. The sample was transferred to the small KAR 130 extruder and extruded through the 1.0 nun screen. The extrudate was air dried overnight and evaluations of the dustiness were taken.

The products of GB 1,433,882 containing disintegrants were rated dusty while the control granules of this invention were rated non dusty.

2. Comparison of Propanil 80 DG with commercial products

Cedar Chemical Corp., 5100 Poplar, Memphis, Tenn. 38137 produces a 50% propanil dispersible granule. Terra International, Inc., Terra Centre 600 Fourth Street, Sioux City, Iowa 51101, produces a 60% propanil dispersible granule.

Propanil 80 DG was compared with commercial products from Cedar and Terra. Suspensibility was measured initially and after storage at 40° C. and 54° C. for 1 to 4 weeks. The results are shown in the following table:

| | | | % Suspensibility | | | | | |
|---|---|---|---|---|---|---|---|---|
| | | | 1 week | | 2 weeks | | 4 Weeks | |
| | % Propanil | Initial | 40° C. | 54° C. | 40° C. | 54° C. | 40° C. | 54° C. |
| Cedar | 50 | 29 | 35.4 | 16.0 | 20.7 | 14.6 | 27.5 | 13.8 |
| Terra | 60 | 41.0 | 21.4 | 16.1 | 27.4 | 7.0 | 14.5 | 6.6 |
| DG #1 | 80 | 89.0 | 91.0 | 88.5 | 88.9 | 88.8 | 89.0 | 88.3 |
| DG #2 | 80 | 89.6 | 91.2 | 89.2 | 90.0 | 89.3 | 87.4 | 88.1 |
| DG #3 | 80 | 91.2 | 91.3 | 88.7 | 90.8 | 87.8 | 90.6 | 86.5 |
| DG #4 | 80 | 91.7 | 90.3 | 86.0 | 87.9 | 83.3 | 88.2 | 86.0 |

Samples DG #1-#4 of this invention were prepared by the procedure of Example 1. Sample #4 used Morwet B instead of Surfactant XN-45S as the wetting agent.

The Cedar product was rated very dusty having approximately 5% by weight of particles less than 45 microns in diameter after attrition. The Terra product was rated dusty. In contrast, two lots of the granules of this invention had 0.184% and 0.239% by weight of particles less than 45 microns in diameter after attrition and were rated non-dusty.

We claim:

1. A process for preparing propanil dispersible granules with less than 0.30 weight percent of particles which are less than 45 microns in diameter after 10 minutes of attrition, comprising the steps of:

a) forming a premix by milling, at a temperature of less than 80° C., one or more surfactants combined with an amount of propanil sufficient to achieve at least 60% propanil content in the dispersible granules, to a particle size of less than 20 microns;

b) adding to said premix less than 25% of a mixture comprising water;

c) mixing until a paste is obtained;

d) granulating said paste; and e) drying the granules.

2. The process of claim 1 wherein the amount of propanil in the forming step is sufficient to achieve at least 80% propanil content in the dispersible granules.

3. The process of claim 1 wherein the mixture comprising water further comprises a wetting agent.

4. The process of claim 1 wherein in the drying step the granules are dried at a temperature of less than 60° C. to a moisture content of less than 2%.

5. The process of claim 1 wherein the paste is granulated by extrusion.

6. A process for preparing propanil dispersible granules, comprising the steps of:

a) forming a premix by milling, at a temperature of less than 80° C., a mixture of propanil, dispersant and flow aid to a particle size between 3 and 15 microns;

b) adding a wetting agent dissolved in 12-20% water (based on the total weight of ingredients of step (a)) to the milled mixture;

c) mixing until a homogeneous, extrudable paste is obtained;

d) extruding the paste obtained in step c) to produce extruded granules;

e) drying the extruded granules at a temperature of less than 60° C. to a moisture content of less than 2%.

7. The dispersible granules produced by the process of claim 1.

8. The dispersible granules produced by the process of claim 6.

* * * * *